United States Patent [19]

Horrobin

[11] Patent Number: 5,594,031

[45] Date of Patent: Jan. 14, 1997

[54] METHODS AND COMPOSITIONS FOR THE TREATMENT OF THE SKIN

[76] Inventor: David F. Horrobin, P.O. Box 818, Kentville, Nova Scotia, Canada, B4N 4H8

[21] Appl. No.: 422,614

[22] Filed: Apr. 13, 1995

Related U.S. Application Data

[63] Continuation of Ser. No. 54,344, Apr. 29, 1993, abandoned, which is a continuation of Ser. No. 912,017, Jul. 10, 1992, abandoned, which is a continuation of Ser. No. 771,800, Oct. 7, 1991, which is a continuation of Ser. No. 560,005, Jul. 27, 1990, which is a continuation of Ser. No. 8,751, Jan. 30, 1987, which is a continuation of Ser. No. 846,093, Mar. 31, 1986, abandoned, which is a continuation of Ser. No. 628,268, Jul. 6, 1984, abandoned.

[30] Foreign Application Priority Data

Jul. 13, 1983 [GB] United Kingdom ............... 83/8912

[51] Int. Cl.$^6$ .................................................. A61K 31/185
[52] U.S. Cl. .................. 514/553; 514/558; 514/864
[58] Field of Search ............................................. 424/153

[56] References Cited

U.S. PATENT DOCUMENTS

| 1,557,758 | 10/1925 | Fulton et al. ............. | 514/844 |
| 1,670,449 | 5/1928 | Hashimoto ................ | 424/358 |
| 3,639,625 | 2/1972 | Shermin .................... | 514/847 |
| 4,328,243 | 5/1982 | Horrobin et al. .......... | 424/301 |
| 4,386,072 | 5/1983 | Horrobin et al. .......... | 424/127 |

FOREIGN PATENT DOCUMENTS

| 0037161 | 7/1981 | European Pat. Off. ............. | 514/844 |
| 1469512 | 2/1967 | France ............................... | 424/317 |
| 2210380 | 7/1974 | France ............................... | 514/847 |
| 0076444 | 9/1982 | Germany ...................... | A61K 7/06 |
| 0085579 | 2/1983 | Germany ...................... | A61K 45/06 |

OTHER PUBLICATIONS

Stedman's Medical Dictionary, 24th edition, 1982 William & Wilkins, pp. 362, 380–382, 1090 & 1268.
Physicians' Desk Reference, PDR 38th edition, 1984, Publisher–Jack & Angel, pp. 878, 879, 1542, 2087 & 2093.
Deguchi et al, 1982, vol. 96, pp. 164567y, Chem. Abs.
Morelle et al, Chem. Abs., 1967, vol. 67, pp. 84768a.
Kriegel, Chem. Abs., 1975, vol. 82, pp. 106400p.
Lancant, Chem. Abs., 1975, vol. 83, pp. 136715h.
Gould Medical Dictionary (4th ed. 1979) p. 16, definition of ache.
Ebling et al. Chapter 14, *Rook's Textbook of Dermatology*, 545–552 (1978).
Reynolds "Lithium Carbonate", *Martindale The Extra Pharmacopoeia*, 1535 (1982).

*Primary Examiner*—Shelley A. Dodson
*Attorney, Agent, or Firm*—Foley & Lardner

[57] ABSTRACT

The invention relates to a method of skin treatment comprising the step of topically applying to skin affected by seborrheic dermatitis an amount of a composition comprising an excipient and from about 1% to 30% lithium ion, said amount being sufficient to reduce sebum production by said skin. The invention also relates to a method of skin treatment, which comprises the step of topically applying to skin affected by seborrheic dermatitis an amount of a composition comprising a topically acceptable excipient and an effective amount of a lithium salt.

9 Claims, No Drawings

METHODS AND COMPOSITIONS FOR THE TREATMENT OF THE SKIN

This application is a continuation of application Ser. No. 08/054,344, filed on Apr. 29, 1993, now abandoned, which is a continuation of application Ser. No. 07/912,017, filed Jul. 10, 1992, now abandoned; which is a continuation of application Ser. No. 07/771,800, filed Oct. 7, 1991, pending; which is a continuation of application Ser. No. 07/560,005, filed July 27, 1990, pending; which is a continuation of application Ser. No. 07/008,751, filed Jan. 30, 1987, pending; which is a continuation of application Ser. No. 06/846,093, filed Mar. 31, 1986, now abandoned; which is a continuation of application Ser. No. 06/628,268, filed Jul. 6, 1984, now abandoned.

SUMMARY

Methods and Compositions for the Treatment of the Skin

Skin conditions associated with excess sebum production and in particular seborrheic dermatitis and dandruff may be treated by the topical application to the affected region of compositions containing an effective amount of a topically acceptable lithium salt.

This invention relates to methods for the treatment of skin conditions associated with excess sebum production as well as to compositions for use in such treatment.

U.S. Pat. No. 3,639,625 discloses topical compositions containing lithium succinate for the treatment of various skin diseases. In particular, it is stated that the compositions may be useful in the treatment of exfoliative dermatitis, vaginal pruritis, heat rash such as diaper rash, contact dermatitis, poison ivy, acne vulgaris, dry skin conditions, burns and abrasions.

I have now found that a variety of topically acceptable lithium salts will reduce the oiliness of the skin surface, apparently due to a reduction in sebum formation. This discovery is particularly surprising in view of the reference in U.S. Pat. No. 3,639,625 to the treatment of dry skin conditions. I have also found that seborrheic dermatitis responds favourably to the application of lithium salts. Moreover, the application of lithium salts to the scalp has been found to give an anti-dandruff effect, dandruff being a condition commonly associated with seborrheic dermatitis.

SUMMARY OF THE INVENTION

Thus, in one aspect the invention provides a method of treatment of skin conditions associated with excess sebum production which method comprises applying to skin affected by such conditions an effective amount of a topically acceptable lithium salt.

Conditions which may be treated according to the invention are those associated with excess sebum production and include oily skin, seborrheic dermatitis and dandruff. Seborrheic dermatitis may also be treated according to the invention even when sebum secretion is not excessive.

Thus in a further aspect the invention provides a method of cosmetic treatment of human skin which method comprises topically applying to oily regions thereof or to regions susceptible to dandruff an effective amount of a cosmetic composition containing a topically acceptable lithium salt.

For treatment according to the invention, and especially for the treatment of oily skin, dandruff or other scalp disorders associated with excess sebum production, the invention further provides cosmetic compositions comprising a topically acceptable lithium salt.

In this further aspect the invention provides a cosmetic composition for topical application to the skin comprising an effective amount of a topically acceptable lithium salt and a cosmetic base.

DETAILED DESCRIPTION OF PREFERRED EMBODIMENTS

It is particularly preferred that the base in the compositions of the invention comprises a cosmetic cleansing composition such as a soap, shampoo or cleansing lotion. Thus, the compositions may take the form of solid or liquid soaps or shampoos (including hair shampoos) containing the lithium salt and one or more natural or synthetic surfactants optionally together with one or more conventional soap or shampoo additives such as perfumes, colouring agents and the like.

Other lithium-containing compositions may also be used in the method according to the invention and examples of such compositions include lipsticks, ointments, creams, solutions, lotions, emulsions, suspensions and powders.

Any topically acceptable lithium salt may be used according to the invention since it is believed that the nature of the anion in the salt is not important. Examples of such salts include lithium chloride, succinate, citrate, acetylsalicylate and orotate.

The compositions for use according to the invention conveniently contain from 0,001 to 30%, and preferably from 1 to 10%, by weight of lithium ions.

The following Examples serve to illustrate compositions which may be used in the method according to the invention (all percentages are by weight):

EXAMPLE 1

Ointment

| | |
|---|---|
| Wool alcohols ointment base (BP) | 92% |
| Lithium succinate | 8% |

EXAMPLE 2

Cream

| | |
|---|---|
| Aqueous cream base | 96% |
| Lithium citrate | 4% |

EXAMPLE 3

Cosmetic Night Cream

| | |
|---|---|
| Cosmetic night cream base | 98% |
| Lithium chloride | 2% |

EXAMPLE 4

Hair Shampoo

| Shampoo base | 95% |
|---|---|
| Lithium succinate | 5% |

EXAMPLE 5

Soap

| Soap base | 97% |
|---|---|
| Lithium orotate | 3% |

EXAMPLE 6

Lipstick

| Lipstick base | 90% |
|---|---|
| Lithium succinate | 10% |

I claim:

1. A method of skin treatment, which comprises the step of topically applying to skin affected by seborrheic dermatitis an amount of a composition comprising a topically acceptable excipient and, as an active ingredient, from about 1 to 30% of lithium ion, said amount being sufficient to reduce sebum production by said skin.

2. A method as claimed in claim 1, wherein said composition comprises a lithium salt selected from the group consisting of lithium chloride, lithium citrate, lithium acetylsalicylate, lithium orotate and lithium succinate.

3. A method as claimed in claim 1, wherein said excipient comprises one selected from the group consisting of a lipstick base, a cosmetic cream base and a cosmetic ointment base.

4. A method as claimed in claim 3, wherein said composition comprises a lithium salt selected from the group consisting of lithium chloride, lithium citrate, lithium acetylsalicylate, lithium orotate and lithium succinate.

5. A method of skin treatment, which comprises the step of topically applying to skin affected by seborrheic dermatitis an amount of a composition comprising a topically acceptable excipient and an effective amount of a lithium salt.

6. A method as claimed in claim 5, wherein said composition comprises a lithium salt selected from the group consisting of lithium chloride, lithium citrate, lithium acetylsalicylate, lithium orotate and lithium succinate.

7. A method as claimed in claim 6, wherein said composition comprises 0.001 to 30% of lithium ions.

8. A method as claimed in claim 5, wherein said excipient comprises one selected from the group consisting of a solid soap base, a liquid soap base, a shampoo base, a lipstick base, a cosmetic cream base and a cosmetic ointment base.

9. A method as claimed in claim 8, wherein said composition comprises a lithium salt selected from the group consisting of lithium chloride, lithium citrate, lithium acetylsalicylate, lithium orotate and lithium succinate.

* * * * *